United States Patent [19]

Schasteen

[11] Patent Number: 5,039,662
[45] Date of Patent: Aug. 13, 1991

[54] PEPTIDE WITH ANTI-METASTASIS ACTIVITY

[75] Inventor: Charles S. Schasteen, University City, Mo.

[73] Assignee: Monsanto, St. Louis, Mo.

[21] Appl. No.: 350,066

[22] Filed: May 10, 1989

[51] Int. Cl.$^5$ .................... A61K 37/02; C07K 7/06
[52] U.S. Cl. ................................ 514/17; 530/330
[58] Field of Search ........................ 530/330; 514/17

[56] References Cited

FOREIGN PATENT DOCUMENTS 0204302 12/1986 European Pat. Off. ............ 530/330
0278781 8/1988 European Pat. Off. ............ 530/330

OTHER PUBLICATIONS

L. Furcht et al., "Peptide Fragments of Fibronectin and Laminin: Role in Cell Adhesion and Inhibition of Experimental Tumor Metastasis", *Development Oncology* 41:43 (1986).
L. T. Furcht et al., "Peptide Fragments of Laminin and Fibronectin Promote Migration (Haptotaxis and Chemotaxis) of Metastatic Cells", *CIBA Foundation Symposium* 108:130 (1984).
J. Graf et al., "Identification of an Amino Acid Sequence in Laminin Mediating Cell Attachment, Chemotaxis, and Receptor Binding", *Cell* 48:989 (1987).
Yukihide Iwamoto et al., "YIGSR, A Synthetic Laminin Pentapeptide, Inhibits Experimental Metastasis Formation", *Science* 238, 1132-1134 (1987).
Makoto Sasaki et al., "Sequence of the cDNA Encoding the Laminin B1 Chain Reveals a Multidomain Protein Containing Cysteine-Rich Repeats", *Proc. Natl. Acad. Sci.,* USA 84:935 (1987).
Jeannette Graf et al., "A Pentapeptide from the Laminin B1 Chain Mediates Cell Adhesion and Binds the 67000 Laminin Receptor", *Biochemistry* 26:6896 (1987).

*Primary Examiner*—Lester L. Lee

[57] ABSTRACT

The invention discloses an acylated pentapeptide that inhibits metastasis activity of malignant cells.

6 Claims, 2 Drawing Sheets

PEPTIDE WITH ANTI-METASTASIS ACTIVITY

BACKGROUND

Laminin is a basement membrane-specific glycoprotein active in promoting cell adhesion, migration, proliferation, neurite outgrowth and differentiation. See Timpl, R. H. et al., *J. Biol. Chem.*, 254:9933 (1979), Engel, J. E. et al., *J. Mol. Biol.* 150:97 (1981), and Kleinman, H.K. et al., *J. Cell. Biochem.* 27:317 (1985). Laminin exhibits numerous biological activities, including promoting the attachment, migration, growth, and differentiation of certain cells, see Graf, J. et al., *Cell* 48:989 (1987). Laminin is composed of 3 chains, A, B1 and B2. The three chains form a cruciform-like shape.

Malignant cells, with laminin receptors on their surfaces, bind and attach more readily to laminin than normal cells. Malignant cell invasiveness involves binding to laminin and the use of specific mechanisms including the production of proteolytic enzymes and the movement of the cells into normal tissues. This process involves the degradation of the basement membrane.

Peptides which have been shown to exhibit inhibition of tumor cell metastasis include the pentapeptide tyrosine-isoleucine-glycine-serine-arginine, as disclosed in European Patent Application Publication No. 0278781, Iwamoto, Y. et al., *Science* 238:1132 (1987) and Graf, J. et al., *Biochemistry* 26:6896 (1987). It would be desirable to discover other effective peptides capable of inhibiting tumor cell invasiveness by inhibiting cell attachment to laminin.

SUMMARY OF THE INVENTION

Figure 1:
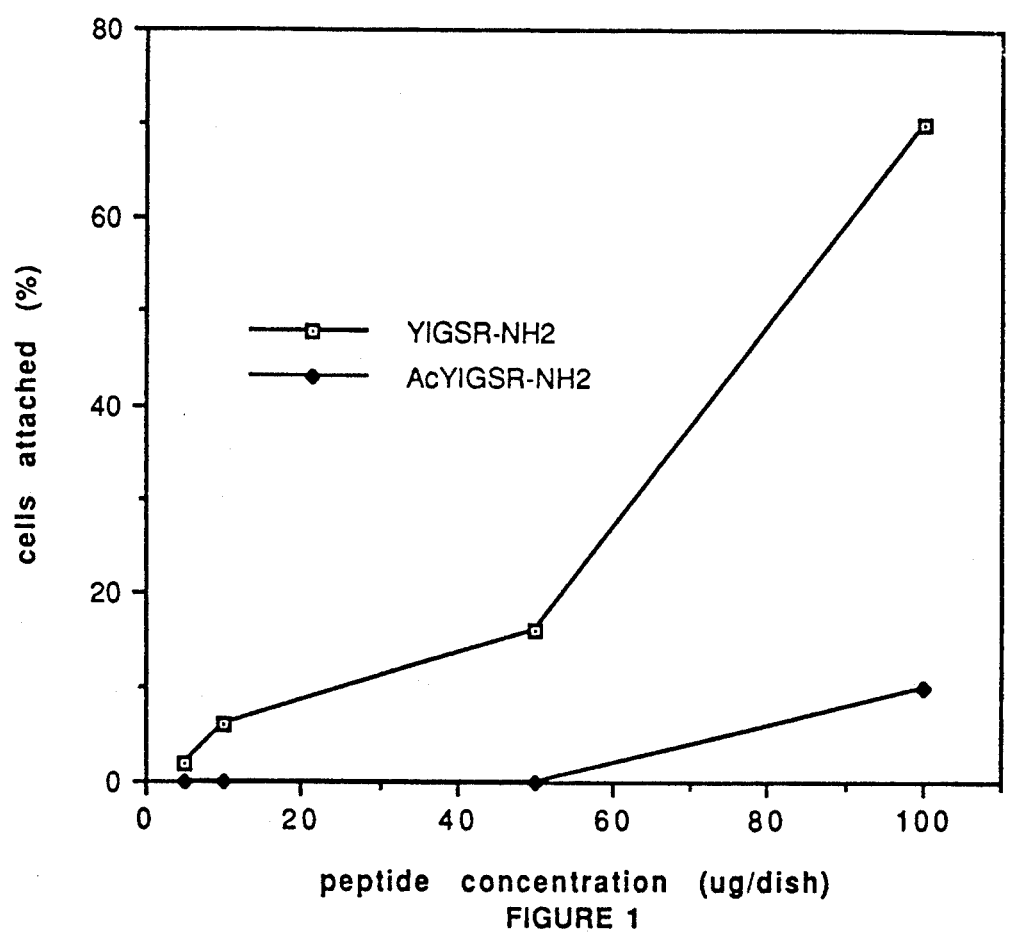
FIG. 1 In vitro cell attachment assays showing the peptide of the invention having cell adhesion activity.

It has been discovered that a peptide having the formula:

AcYIGSR-NH2, or a pharmaceutically acceptable salt thereof, exhibits antimetastasis activity. The peptide blocks cellular adhesion, and melanoma cell colonization. The peptide should be effective in blocking attachment and metastasis of a variety of cell types including breast carcinoma, epidermal carcinoma, muscle line melanoma, epidermal line neuroblastoma x glioma, chondrocytes, human skin fibroblasts, bovine osteoblasts and fibrosarcoma.

The one-letter symbols "Y", "I", "G", "S" and "R" refer to the amino acids L-tyrosine, L-isoleucine, L-glycine, L-serine and L-arginine respectively. "Ac" refers to acetyl

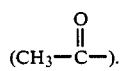

$$(CH_3-\overset{\overset{\displaystyle O}{\|}}{C}-).$$

Non-toxic pharmaceutical salts may be prepared by reaction of the peptide with inorganic or organic acids. The resulting salts maintain the biological activity of the peptide. Examples of satisfactory acids are hydrochloric acid, nitric acid, phosphoric acid, tartaric acid and acetic acid.

The peptide of this invention interacts with the laminin receptors on a malignant cell so that it cannot bind to laminin, thereby blocking the binding of the malignant cell to laminin and inhibiting the destructive invasiveness of the malignant cell. The peptide of the invention acts by blocking cell adhesion, and blocking laminin-mediated adhesion.

The peptide of the invention is synthesized by the classical solid phase synthesis procedure of Merrifield, (*J. Am. Chem. Soc.* 85:2149 (1963) as described by Stewart and Young (Solid Phase Peptide Synthesis, 2nd Ed. (1984), Pierce Chemical Company, Rockford, Ill.). Acylation is carried out on an amide resin by addition of acetic anhydride in a suitable solvent. Examples of suitable solvents including acetone, dioxane and methylene chloride.

The peptide of the invention may be used in a variety of therapeutic and pharmaceutical applications relating to malignant tumor cells. Typically, the peptide is administered as a pharmaceutical composition comprising an excipient. The pharmaceutical composition may be prepared by any of the known procedures as described in Remington's Pharmaceutical Sciences, Mack Publishing Company, Eaton, Pa. 16th Ed., 1980. Excipients may include sterile water, saline solution and buffered saline including buffers like phosphate or acetate, sodium chloride or sucrose as pressure adjusting agents, and antioxidants such as ascorbic acid, or any acceptable combinations thereof. The pharmaceutical composition may be in various forms like tablets and solutions and be administered by various routes including orally, nasally, and parenterally (including intravenously, intramuscularly, subcutaneously and intraperitoneally). The dose range will vary depending on variables like the patient's age, weight, condition, and route of administration. Typically, dose range is from 0.001 to 100 mg of active substance per kilogram body weight. Preferably the range is from 0.01 to 50 mg of active substance per kilogram body weight.

DESCRIPTION OF THE PREFERRED EMBODIMENTS

The following examples illustrate specific embodiments of the invention described herein.

EXAMPLE 1

The Tyrosine-Isoleucine-Glycine-Serine-Arginine (YIGSR-NH$_2$) peptide, is synthesized by the classical solid phase synthesis procedure of Merrifield (*J. Am. Chem. Soc.* 85, 2149-54 (1963) as described by Stewart and Young (Solid Phase Peptide Synthesis, 2nd Ed. (1984) Pierce Chemical Co., Rockford, Ill.) on an automated Model Applied Biosystems synthesizer, using methylbenzhydrozylamine (methylBHA) resin (Applied Biosystems Inc., Foster City, Calif.). Acylation of the peptide is done (on the resin) by addition of a 10-fold molar excess (with respect to free amino terminus of peptide) of acetic anhydride (Pierce Chemical Co.) in methylene chloride for 30 minutes at room temperature. Deprotection and release of the peptides from the solid-phase support matrix is accomplished by treating the protected peptide on the resin with anhydrous HF containing 10% anisole for 1-2 hours at 0° C. Deprotection reagents are removed by extraction with ethyl acetate, the peptide dissolved in 30% aqueous acetic acid, and the solution is filtered through a sintered glass (coarse) Buechner funnel to remove the resin.

EXAMPLE 2

HT-1080 cells from a human fibrosarcoma (Rasheed, S. et al., *Cancer* (Philadelphia) 33:1027 (1974) are maintained in Dulbecco's modified Eagle's medium (DMEM) supplemented with 10% fetal calf serum. After the cells are grown to 80% confluency, they are washed with 0.02M phosphate buffer, pH 7.4, without $Ca^{2+}$ and $Mg^{2+}$ and detached with a solution of 0.025% trypsin plus 0.025% ethylenediaminetetraacetic acid (EDTA; GIBCO). The cells are then pelleted by lowspeed centrifugation and resuspended in Eagle's minimal essential medium (EMEM) containing 0.02% bovine serum albumin (BSA, Sigma Chemical Co., St. Louis, Mo.). Cell attachment assays are performed as described in Klebe, R. J. *Nature* (London) 250:248 (1974), on tissue culture plastic substrates by using 16-mm Falcon tissue culture wells (Fisher Scientific Co., Pittsburg, Pa.) incubated with various peptides or with laminin in 1 mL of EMEM containing 0.02% BSA for 1 or 2 hours at 37° C. Cells ($10^5$ in 0.1 1 mL) are added to the wells, and the solution is incubated for an additional 1 hour at 37° C. in 95% air and 5% $CO_2$. Subsequently, the wells are rinsed 3 times with 1 mL of phosphate-buffered saline (PBS) to remove unattached cells. Attached cells are trypsinized and counted electronically (Coulter, ZBI). The attachment assays are carried out in the presence of cycloheximide (25 mg/mL) to minimize the production of endogenous attachment proteins. Each peptide is tested in duplicate dishes and each assay is repeated 6 times. The variation between samples in different assays is <15%.

To test the inhibition of attachment to laminin by the peptides, bacteriological petri dishes (35 mm) are coated with 5 mg of laminin which is allowed to air-dry onto the dishes overnight. Prior to the addition of the cells, varying concentrations of the peptide solubilized in serum-free EMEM containing 0.05% BSA are added to each dish. The attachment assay is then carried out as described above. Each dish contained a final volume of 1.0 mL and each assay is performed in duplicate with each peptide assayed nine times. In vitro cell attachment assays, as shown in FIG. 1, show the peptide of the invention having cell adhesion activity.

EXAMPLE 3

Figure 2:
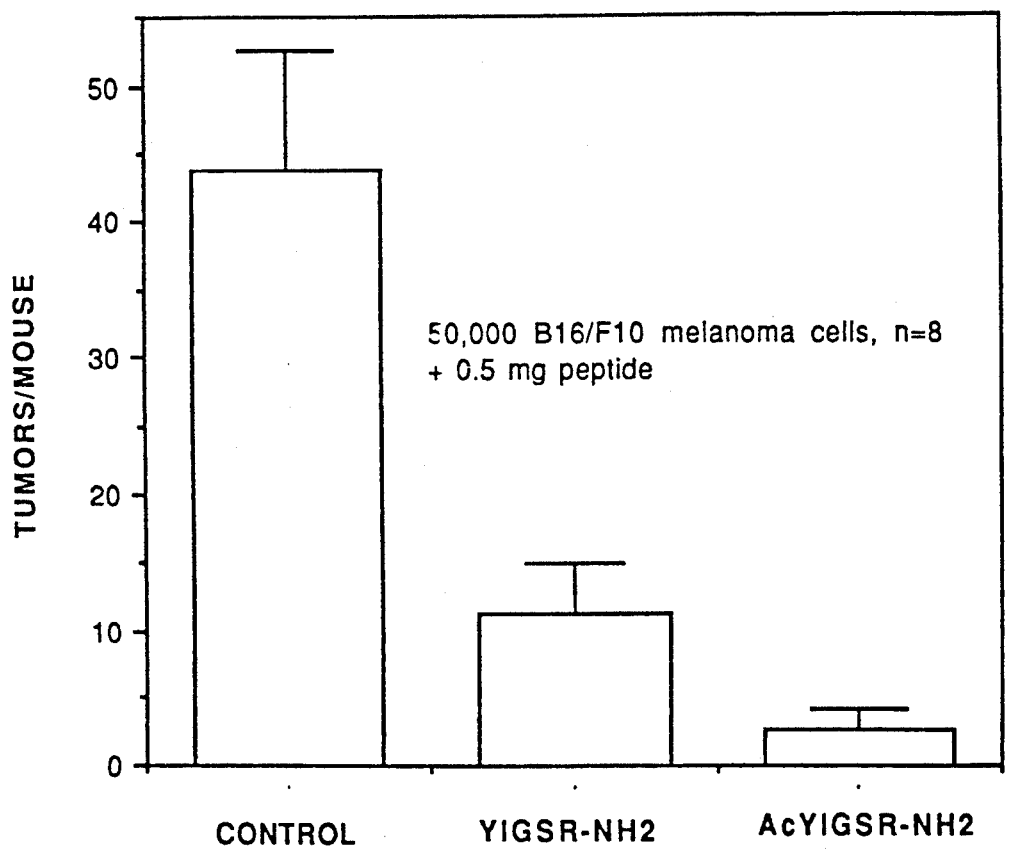
FIG. 2 In vivo antimetastic data showing the peptide of the invention being at least twice as effective as linear YIGSR-NH$_2$.

B16F10 melanoma cells, obtained from I. J. Fidler, M. D., Anderson Hospital, Houston, Tex., are propagated under standard culture conditions. The lung tumor colonization assay is carried out as described in Fidler, I. J., *Nature* (London) (*New Biol*) 242:148 (1973). Peptides are dissolved at 5 mg/mL in PBS and are filter-sterilized. The suspension of B16F10 cells ($5 \times 10^5$) in 0.1 mL of DMEM is mixed with 0.1 mL of the peptide, (or 0.1 ml PBS in Control) incubated for 5 minutes at room temperature, and then injected into the tail vein of syngeneic C57BL/6 female mice (Jackson Labs., Bar Habor, Me.) at 6 weeks of age. Each treatment and control group consists of eight mice. Three weeks after the injections, the mice are killed and the number of pulmonary tumors on the surface of the lungs counted. FIG. 2 shows that AcYIGSR-$NH_2$, the peptide of the invention is at least twice as effective as YIGSR-$NH_2$.

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included therein.

What is claimed is:

1. A peptide of the formula:
    AcYIGSR—$NH_2$ in which Ac is acetyl, or a pharmaceutically acceptable salt thereof.
2. The peptide of claim 1 of the formula:
    AcYIGSR—$NH_2$.
3. The peptide of claim 1 which is a pharmaceutically acceptable salt of the peptide of the formula:
    AcYIGSR—$NH_2$.
4. A pharmaceutical composition comprising a pharmaceutically acceptable excipient and a therapeutically effective amount of a peptide of the formula:
    AcYIGSR—$NH_2$ in which Ac is acetyl, or a pharmaceutically acceptable salt thereof.
5. The pharmaceutical composition of claim 4 in which the peptide is of the formula:
    AcYIGSR—$NH_2$.
6. The pharmaceutical composition of claim 4 in which the peptide is a pharmaceutically acceptable salt of the peptide of the formula:
    AcYIGSR—$NH_2$.

* * * * *